United States Patent [19]
Khalili

[11] Patent Number: 5,997,581
[45] Date of Patent: Dec. 7, 1999

[54] HIP STEM CEMENT SPACER

[75] Inventor: Farid Bruce Khalili, Chestnut Hill, Mass.

[73] Assignee: Johnson & Johnson Professional, Inc., Raynham, Mass.

[21] Appl. No.: 08/998,882

[22] Filed: Dec. 29, 1997

[51] Int. Cl.[6] .................................................. A61F 2/36
[52] U.S. Cl. ........................... 623/23; 623/18; 606/92; 606/93; 606/94; 606/95
[58] Field of Search .................. 623/18, 23; 411/148; 606/92, 93, 94

[56] References Cited

U.S. PATENT DOCUMENTS

| | | | |
|---|---|---|---|
| 3,793,650 | 2/1974 | Ling et al. | 3/1 |
| 4,293,962 | 10/1981 | Fuson | 3/1.9 |
| 4,466,435 | 8/1984 | Murray | 128/303 |
| 4,576,152 | 3/1986 | Muller | 128/92 |
| 4,625,722 | 12/1986 | Murray | 128/92 |
| 4,718,909 | 1/1988 | Brown | 623/16 |
| 4,783,192 | 11/1988 | Wroblewski et al. | 623/16 |
| 4,944,759 | 7/1990 | Mallory | 623/22 |
| 5,057,101 | 10/1991 | Dorr et al. | 623/23 |
| 5,108,439 | 4/1992 | Morscher et al. | 623/18 |
| 5,197,990 | 3/1993 | Lawes et al. | 623/23 |
| 5,340,362 | 8/1994 | Carbone | 623/23 |
| 5,383,932 | 1/1995 | Wilson et al. | 623/16 |
| 5,658,351 | 8/1997 | Dudasik et al. | 623/23 |
| 5,662,657 | 9/1997 | Carn | 606/95 |
| 5,755,793 | 5/1998 | Smith | 623/16 |

FOREIGN PATENT DOCUMENTS

| | | | |
|---|---|---|---|
| 0 216 489 A1 | 4/1987 | European Pat. Off. | 2/30 |
| 9725940 | 7/1997 | WIPO . | |

*Primary Examiner*—David H. Willse
*Assistant Examiner*—Suzette J. Jackson
*Attorney, Agent, or Firm*—Nutter, McClennen & Fish, LLP

[57] ABSTRACT

A spacer includes a body having a first end, a second end, and an aperture open at the first end and at the second end. The spacer can be an element of a prosthetic joint component system that further includes a cement injection nozzle insertable through the aperture in the spacer and a sleeve disposable around at least a portion of the nozzle.

9 Claims, 2 Drawing Sheets

HIP STEM CEMENT SPACER

BACKGROUND OF THE INVENTION

Disease and/or trauma cause deterioration of natural joints of the human body. Replacement of natural joints with joint prostheses can distinctly enhance the quality of life of an individual affected by such joint conditions. Various joint prostheses are known. Among the more common joint prostheses are those that replace all or part of the natural knee and hip joints.

Components of joint prostheses must be implanted and secured within existing bone. In the case of hip arthroplasty, a surgical technique in which the hip joint is replaced by a prosthetic joint, a cavity is prepared in a proximal portion of the patient's femur to receive a femoral stem (a portion of a prosthetic hip joint). Other joint replacement surgical techniques require the formation of similar cavities within existing bone for the installation of various prosthesis components.

Once such a cavity is prepared, the prosthesis component may be secured within the cavity by a number of techniques. For example, the prosthesis component may be cemented within the cavity, or it can be installed through mechanical fixation by a friction fit or the use of a fixation device.

When cement is used to secure a prosthetic component in place, it is usually desirable to create an even cement mantle around the component. One way to ensure a uniform cement mantle is to center the prosthetic component within the target cavity with the assistance of a mechanical guide secured to the prosthetic component. Such guides are commonly referred to as "spacers" or "centralizers." Known spacers for hip stems, for example, are snugly fitted to the distal end of the hip stem prior to the stem being plunged into a reamed femoral canal filled with bone cement.

Although the known spacers can be generally successful in centralizing the stem within the femoral canal, the configuration of the spacers and the techniques for using them cause a variety of problems with respect to the integrity of the cement mantle and the bond between the cement mantle and the prosthetic components. For example, depending on the bone cement selected, even a short delay from the time the cement is prepared and deposited into the canal, to the time that the stem and spacer are inserted therein, can allow the cement to cure or harden enough so that a sub-optimal bond between the cement and the spacer occurs. Additionally, the spacer can divide the cement mantle into three or four sections beyond the distal tip of the stem in a way such that the separated sections do not bond together.

Furthermore, as a mated stem and spacer are inserted into a bone cement filled canal, the spacer tends to drag air, in the form of small bubbles, from the surface of the cement at the point of insertion all the way to the final resting point of the spacer. The bubbles, many of which become trapped in the cement as it hardens, create discontinuities at the interface between the spacer/stem and cement that can lead to debonding. Because the spacer is at the distal end of the stem, bubbles are at the distal end; and the distal end is where the highest cement/stem interface stresses are produced. Also, when the cement hardens, it is likely that the spacer will not bond with the cement. Thus, not only do known techniques create the precursor of bonding failure, they do so in the most vulnerable location.

Therefore, it is desirable to provide additional structures and techniques that can be easily implemented and that address the challenges of hip stem fixation, and more particularly the problems associated with creating a robust cemented fixation.

SUMMARY OF THE INVENTION

The present invention provides apparatus and procedure that improve cement fixation of prosthetic implants, such as femoral stems.

A spacer is provided that includes a body having a first end, a second end, and an aperture open at the first end and at the second end. The spacer can be an element of a prosthetic joint component system that further includes a cement injection nozzle insertable through the aperture and a sleeve disposable around at least a portion of the nozzle and which is slidable with respect thereto.

In an exemplary method, a bone cavity is prepared to receive a prosthetic implant. A spacer, slidably disposed on a cement nozzle, is inserted into the bone cavity and positioned with a sleeve. The bone cavity is filled with bone cement and the prosthetic implant is engaged with the spacer.

BRIEF DESCRIPTION OF THE DRAWINGS

Other features and benefits of the invention can be more clearly understood with reference to the specification and the accompanying drawings in which.

DETAILED DESCRIPTION OF THE INVENTION

Figure 1:
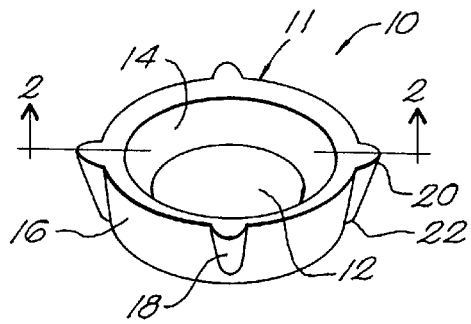
FIG. 1 is a perspective view of a spacer in accordance with the invention.

FIG. 1 is a perspective view of a spacer 10 in accordance with the invention. The spacer 10 can function as a stand-alone device that replaces in an enhanced manner known spacers, or it can function as a component of a unique cement system and method described in greater detail below.

The spacer 10 includes a body 11 having opposing first and second ends, wherein the body defines an aperture 12 open at both ends. In the illustrated embodiment of FIG. 1, the aperture 12 is generally circular and the body 11 is symmetric about a center point of the aperture. The generally ring-like, toroidal, or frustroconical body 11 includes an inner facing wall 14 and an outer facing wall 16.

Protuberances 18 extend from the outer facing wall 16. The protuberances 18 can be evenly spaced, approximately 90 degrees apart as shown, or unevenly spaced. Although four protuberances 18 are shown, the spacer 10 can include less than four or more than four protuberances.

Each protuberance 18 has a first end 20 and a second end 22. The first and second ends 20, 22 of the protuberances 18 can extend beyond the first and/or second end of the body 11, be substantially co-planar with the first and/or second end of the body, or not extend as far as the first and/or second end of the body. In the illustrated embodiment, the first end 20 of each protuberance 18 extends beyond a first end of the body 11, and the second end 22 of each protuberance does not extend as far as a second end of the body.

The protuberances 18 define an outer circumference of the spacer 10 that is greater than the circumference of the outer facing wall 16 of the body 11. The protuberances 18 can be simple bumps or elongate elements and they can be hard and rigid or soft and resilient. In the illustrated embodiment, the protuberances 18 are rigid, elongate structures having a rounded outer face and that are tapered so that the first end of the protuberance is wider than the second end.

Figure 2:
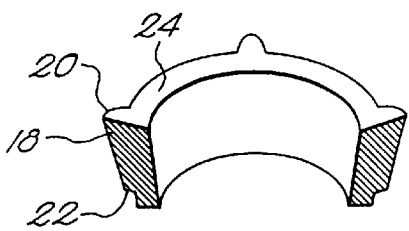
FIG. 2 is a sectional view of the spacer of FIG. 1, taken along line 2—2.

FIG. 2 is a sectional view of the spacer 10 of FIG. 1, taken along line 2—2. In this view, an inwardly sloping first or proximal end 24 of the body 11 leads to the aperture 12 through the body. As shown, the body 11 is tapered or frustroconical and the aperture 12 has a greater diameter at one end of the body than at the other end.

Various embodiments of the spacer 10 include a body 11 having an outer facing wall 16 that is cylindrical or tapered in combination with an inner facing wall 14 that is cylindrical or tapered.

Figure 3:
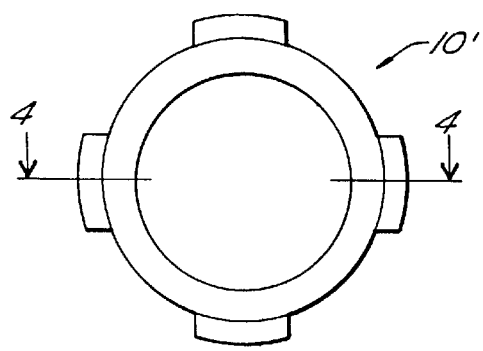
FIG. 3 is a plan view of an alternative embodiment of the spacer of FIGS. 1 and 2.

FIG. 3 illustrates an embodiment of a spacer 10' having four evenly spaced-apart protuberances 18' that have a generally rectangular profile when viewed from an end of the spacer.

Figure 4:
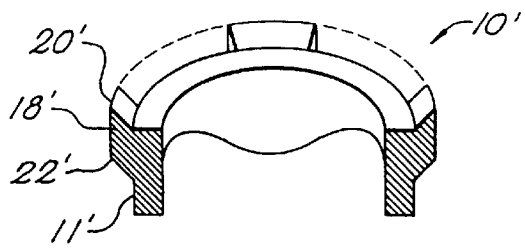
FIG. 4 is a sectional view of the spacer of FIG. 3, taken along line 4—4.

FIG. 4 is a sectional depiction of the spacer 10' shown in FIG. 3. In this view, one end of the body is shown to have a substantially flat end face that is uniform in height. The protuberances 18' have first ends 20' that extend beyond the flat end face about the same distance (dashed line). The protuberances 18, 18' can include sharp first ends 20, 20' or end portions. As shown in FIG. 4, the body 11' is not uniform in length, and the lower end of the body (as illustrated) defines an end face that is not planar.

Figure 5:
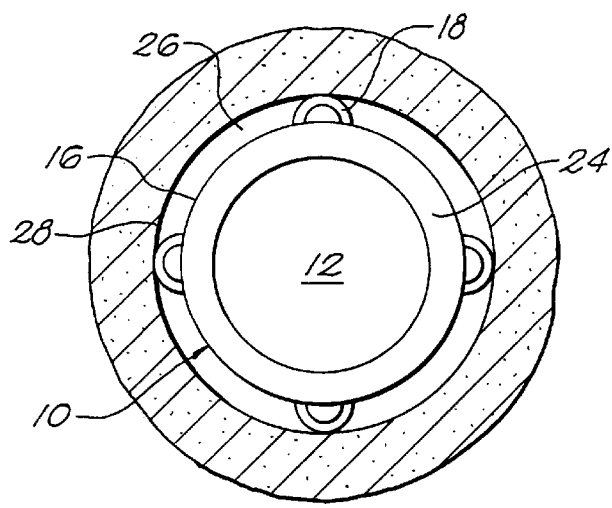
FIG. 5 is a transverse sectional view of a reamed femur, wherein a spacer is shown within the reamed femoral canal.

Referring now to FIG. 5, an exemplary spacer 10, selected from a group of spacers having different outer and inner diameters, is shown positioned within a reamed femoral canal 26. The spacer 10, illustrated as viewed from the distal end of the spacer, is placed into the reamed canal in an orientation so that the first end of the spacer and the aperture face the open mouth of the reamed canal.

Each of the protuberances 18 are contact with an inner face 28 of the reamed canal. Thus, the outer wall 16 of the body is spaced away from and not in contact with the inner face 28, and the spacer 10 is centered within the femoral canal 26. Gaps between the outer wall 16 of the body and the inner face 28 of the reamed canal 26 should be noted as they provide a path for bone cement to flow around and envelop the spacer as will be described in greater detail below.

Figure 6:
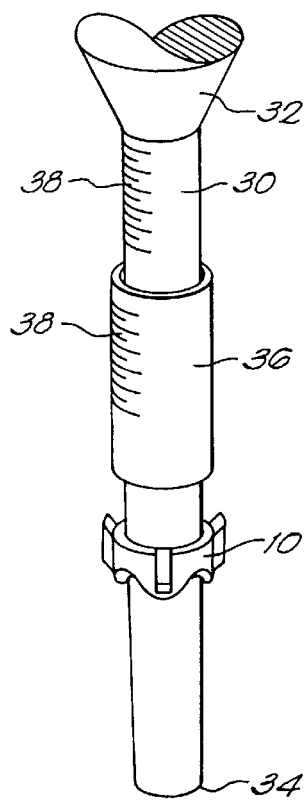
FIG. 6 is a perspective view of a cement system in accordance with the invention.
Figure 8:
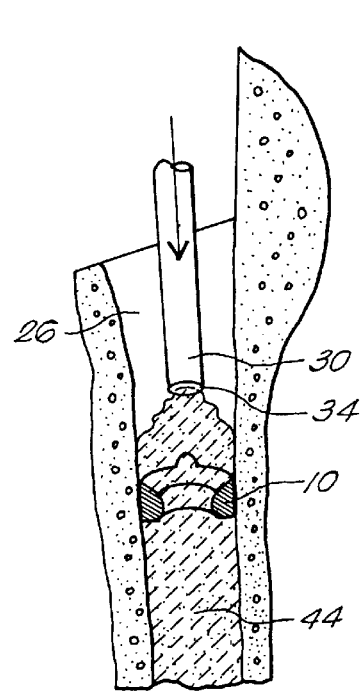
FIG. 8 illustrates retrovert cement injection within the femur.

FIG. 6 illustrates a cement system in accordance with the invention in association with an exemplary spacer 10. The cement system includes a cement delivery nozzle 30 having a proximal end 32 that can be placed in communication with a supply of bone cement (not shown), and a distal end 34 that is insertable through the aperture 12 of the spacer 10 and from which bone cement can issue as illustrated in FIG. 8. The nozzle 30 can have a length greater than the length of a prosthetic hip stem 46 (shown in FIG. 8). A sleeve 36 surrounds at least a portion of the nozzle 30 and is slidable with respect thereto. The sleeve 36 is useful for positioning the spacer 10, and more particularly for pushing it toward the distal end 34 of the nozzle 30. Measurement indicia 38 can be provided on the sleeve 36 and on the nozzle 30 to help gauge insertion depth of the nozzle and of the spacer 10 within the reamed canal 26.

Figure 7:
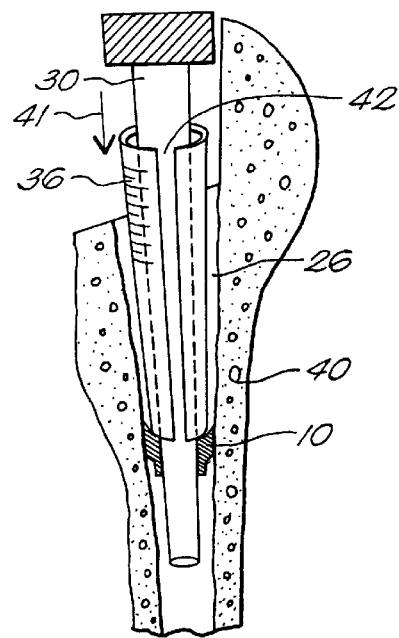
FIG. 7 is a sectional illustration of a femur showing the cement system being positioned in preparation for cement deposition.

FIG. 7 illustrates the cement delivery system and spacer positioned within a reamed canal 26 of a femur 40. In an exemplary method, an appropriately dimensioned spacer 10 is placed onto the nozzle 30. The nozzle 30 is then inserted into the reamed canal 26. The sleeve 36 is used to push the spacer 10 toward the distal end 34 of the nozzle 10 (in the direction shown by arrow 41) until the spacer is at a selected depth within the reamed canal 26. Typically, the spacer 10 is pushed into the reamed canal 26 until the protuberances 18 of the spacer contact the inner face 28 of the reamed canal. When the spacer 10 is at the selected depth, the sleeve 36 is removed from the nozzle 30 and from the femur 40. A longitudinal discontinuity 42 in the sleeve 36 can be provided to allow the sleeve to be removed from the nozzle 30 without removing the nozzle from the spacer 10 or removing the nozzle from other cement delivery apparatus.

FIG. 8 illustrates an exemplary procedural step, wherein cement 44 is ejected from the open distal end 34 of the nozzle 30 under pressure to fill the reamed canal 26 in a retrovert manner. As cement 44 fills the reamed canal, and flows into the spaces between the inner face 28 and the canal, the nozzle 30 is gradually withdrawn from the spacer 10 that remains substantially or completely unmoved from its selected insertion position and depth. The sleeve 36 can be used to hold the spacer 10 in place so that cement back pressure does not dislodge the spacer. Additionally, sharp edges on the protuberances 18, 18' can dig into the bone to help hold the spacer 10 in place. Once the nozzle 30 is disengaged from the spacer 10 (now fully enveloped in uncured bone cement 44), additional bone cement is added in a retrovert manner as desired by the surgeon.

Figure 9:
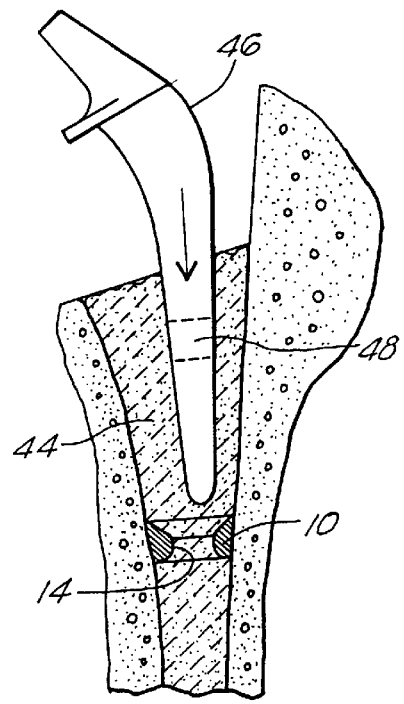
FIG. 9 depicts a femoral stem being passed through cement toward the spacer.

Before the cement 44 cures, an elongate prosthetic component, such as a femoral stem 46, is passed through uncured cement 44 toward the spacer 10 as shown in FIG. 9. The stem 46 is inserted into the spacer 10 until it is firmly seated. A sloping or chamfered proximal end 24 of the body (FIG. 2) helps to guide the stem 46 into the body 11 and center it therein. The stem 46 and the spacer 10 are dimensioned so that a central region 48 of the stem 46 binds in an interference fit with the inner facing wall 14 of the spacer 10. The stem 46 is centered and held in place at a selected depth until the cement 44 cures.

The stem 46 alone drags few, if any, bubbles into the uncured cement 44 during stem insertion into the spacer 10. When the cement cures, a very high quality, crack resistant mantle is provided to hold the stem in place. The cement mantle has few discontinuities, especially at the high-stress zone around the distal tip of the stem. Because the cement is deposited into the canal after the spacer is positioned within the canal, the potential is greater for full bonding between the cement and the spacer because the cement exiting the dispensing nozzle is in its most liquid form, and grooves caused by pushing a spacer through partially hardened cement are eliminated. Discontinuities associated with the stem, if any, are in the mid-shaft area where the stress on the cement is the lowest.

Although the invention has been shown and described with respect to exemplary embodiments thereof, various other changes, omissions and additions in form and detail thereof may be made therein without departing from the spirit and scope of the invention.

What is claimed is:

1. A prosthetic joint component system for use with an elongate prosthetic component having a proximal end region, a distal end region, and a central region between the proximal end region and the distal end region, the prosthetic joint component system comprising:

a body having a first end and a second end, the body defining an aperture open at the first end and at the second end, the aperture having a diameter greater than that of the distal end region and less than that of the proximal end region of the elongate prosthetic component, wherein the elongate prosthetic component is receivable through the aperture so that the body binds against the elongate prosthetic component in the central region of the elongate prosthetic component, wherein the aperture defined by the body is generally circular, wherein the body is symmetric about a center point of the aperture, and wherein the body is generally toroidal and includes an inner facing wall and an outer facing wall;

a plurality of protuberances extending from the outer facing wall, wherein the plurality of protuberances are evenly spaced, wherein the protuberances include sharp edges, wherein each of the protuberances includes a first end and a second end, and wherein at least one of the first end and second end of each protuberance extends beyond one of the first end and second end of the body, respectively; and a cement injection nozzle having an open distal end portion insertable through the aperture, the nozzle including measurement indicia.

2. The prosthetic joint component system of claim 1, further comprising a sleeve disposable around at least a portion of the nozzle.

3. The prosthetic joint component system of claim 2, wherein the sleeve is provided with measurement indicia.

4. The prosthetic joint component system of claim 2, wherein the sleeve includes a longitudinal discontinuity and wherein the sleeve is flexible.

5. A prosthetic joint component system for use with an elongate prosthetic component having a proximal end region, a distal end region, and a central region between the proximal end region and the distal end region, the prosthetic joint component system comprising:

a body having a first end and a second end, the body having an inner facing wall defining an aperture open at the first end and at the second end, the aperture having a diameter greater than that of the distal end region and less than that of the proximal end region of the elongate prosthetic component, and an outer facing wall from which a plurality of protuberances extend in a spaced-apart relationship;

a cement injection nozzle insertable through the aperture; and a sleeve disposable around at least a portion of the nozzle and slidable with respect thereto.

6. A method of using a prosthetic joint component system comprising the steps of:

preparing a bone cavity to receive a prosthetic implant having a proximal end region, a distal end region, and a central region between the proximal end region and the distal end region;

providing a body having a first end and a second end, the body having an inner facing wall defining an aperture open at the first end and at the second end, the aperture having a diameter greater than that of the distal end region and less than that of the proximal end region of the elongate prosthetic component, and an outer facing wall from which a plurality of protuberances extend in a spaced-apart relationship;

inserting the body into a bone cavity;

depositing bone cement into the bone cavity; and inserting the prosthetic implant through the aperture until the distal end of the prosthetic implant extends distally beyond the body, and the central region of the implant binds against the inner facing wall of the body.

7. A method of using a prosthetic joint component system comprising the steps of:

preparing a bone cavity to receive a prosthetic implant having a proximal end region, a distal end region, and a central region between the proximal end region and the distal end region;

providing a body having a first end and a second end, the body having an inner facing wall defining an aperture open at the first end and at the second end, the aperture having a diameter greater than that of the distal end region and less than that of the proximal end region of the elongate prosthetic component, and an outer facing wall from which a plurality of protuberances extend in a spaced-apart relationship;

inserting the body into a bone cavity;

depositing bone cement into the bone cavity;

inserting the prosthetic implant through the aperture until the distal end of the prosthetic implant extends distally beyond the body, and the central region of the implant binds against the inner facing wall of the body;

providing a nozzle;

providing a sleeve;

surrounding the nozzle with the sleeve;

inserting a portion of the nozzle through the aperture in the body; and engaging the body with the sleeve.

8. The method of claim 7, further comprising the step of pushing the body toward the distal end of the nozzle.

9. The method of claim 7, further comprising the step of using the sleeve to holding the body at a selected point along the nozzle.

* * * * *